(12) United States Patent
Wakabayashi et al.

(10) Patent No.: US 10,914,406 B2
(45) Date of Patent: Feb. 9, 2021

(54) TUBE HOLDER

(71) Applicant: ATOM MEDICAL CORPORATION, Tokyo (JP)

(72) Inventors: Keisuke Wakabayashi, Saitama (JP); Masaaki Oohashi, Saitama (JP); Yoshiyuki Komiyama, Saitama (JP); Ichiro Matsubara, Tokyo (JP)

(73) Assignee: Atom Medical Corporation, Tokyo (JP)

( * ) Notice: Subject to any disclaimer, the term of this patent is extended or adjusted under 35 U.S.C. 154(b) by 46 days.

(21) Appl. No.: 16/509,223

(22) Filed: Jul. 11, 2019

(65) Prior Publication Data

US 2019/0353281 A1 Nov. 21, 2019

Related U.S. Application Data

(63) Continuation of application No. PCT/JP2017/018299, filed on May 16, 2017.

(30) Foreign Application Priority Data

Jan. 12, 2017 (JP) ................................ 2017-003216

(51) Int. Cl.
*F16L 3/10* (2006.01)
*F16L 3/227* (2006.01)
(Continued)

(52) U.S. Cl.
CPC ............. *F16L 3/1041* (2013.01); *F16L 3/227* (2013.01); *F16L 3/237* (2013.01); *F16B 2/10* (2013.01)

(58) Field of Classification Search
CPC ......... F16L 3/1041; F16L 3/227; F16L 3/237; F16L 3/10; F16L 3/1008; F16L 3/1025;
(Continued)

(56) References Cited

U.S. PATENT DOCUMENTS 3,312,434 A * 4/1967 Simon ................ A61B 1/00117
248/62
3,456,262 A * 7/1969 Coon ...................... B42F 1/006
24/501
(Continued)

FOREIGN PATENT DOCUMENTS

JP S43-090298 Y 1/1968
JP H02-024183 U 2/1990
(Continued)

*Primary Examiner* — Terrell L McKinnon
*Assistant Examiner* — Michael McDuffie
(74) *Attorney, Agent, or Firm* — Brinks Gilson & Lione

(57) ABSTRACT

A tube holder includes at least a set of clamping members having circular arc-shaped clamping concave portions, a spindle pivotably supporting end portions on one side along the circular arcs of the clamping members in a state where the clamping concave portions facing curvature center sides of the respective circular arcs face each other, and a biasing member pivoting and biasing end portions of the other side along the circular arc of the clamping member in a direction of mutual approaching. The clamping member is formed such that an inscribed circle formed between facing surfaces of the clamping concave portions is smaller than a virtual circle formed by extension of the circular arcs of the clamping concave portions in a state where a space between the other end portions is closed and the clamping concave portions are disposed on the same virtual circle formed by extension of the circular arcs in a state during opening and closing where the clamping members are pivoted and the end portions on the other side are moved close to and away from each other.

8 Claims, 6 Drawing Sheets

(51) Int. Cl.
*F16L 3/237* (2006.01)
*F16B 2/10* (2006.01)

(58) Field of Classification Search
CPC ..... F16L 3/1033; F16L 3/1075; F16L 3/1083; F16L 3/1091; F16L 3/22; F16B 2/10
USPC ............ 248/689, 65, 68.1, 74.1, 74.2, 74.4, 248/229.13, 229.16, 229.23, 229.26, 248/231.51, 231.81, 58, 75, 51
See application file for complete search history.

(56) References Cited

U.S. PATENT DOCUMENTS

| | | | | |
|---|---|---|---|---|
| 5,118,215 A * | 6/1992 | Freier | .............. | F16L 3/1203 248/74.2 |
| 5,277,387 A * | 1/1994 | Lewis | .............. | F16L 3/1041 24/482 |
| 5,280,866 A * | 1/1994 | Ueki | .............. | F16L 3/233 248/74.2 |
| 5,527,006 A * | 6/1996 | Stith | .............. | A47G 33/10 248/229.13 |
| 5,535,970 A * | 7/1996 | Gobbi | .............. | F16L 3/13 24/557 |
| 5,572,776 A * | 11/1996 | Murphy | .............. | F16B 2/10 24/487 |
| 5,769,556 A * | 6/1998 | Colley | .............. | B62H 3/02 24/335 |
| 7,766,313 B2 * | 8/2010 | Panosian | .............. | B25B 5/163 269/37 |
| 7,770,859 B2 * | 8/2010 | Costabel | .............. | F16L 3/10 248/316.5 |
| 8,079,552 B2 * | 12/2011 | Sweigard | .............. | F16L 3/13 248/74.2 |
| 8,272,612 B2 * | 9/2012 | Thorpe | .............. | A24F 13/22 248/316.7 |
| 10,429,147 B2 * | 10/2019 | Williams | .............. | F16B 2/10 |
| 10,495,953 B2 * | 12/2019 | Calhoun | .............. | G03B 17/561 |
| 2003/0230678 A1 * | 12/2003 | Bellmore | .............. | F16L 3/1203 248/68.1 |
| 2007/0289075 A1 | 12/2007 | Gopalan | | |
| 2010/0019107 A1 * | 1/2010 | McCloud | .............. | A61M 16/0875 248/83 |
| 2013/0174838 A1 | 7/2013 | Youngblood | | |
| 2016/0029825 A1 * | 2/2016 | Perrin | .............. | A47B 61/003 223/85 |
| 2017/0292634 A1 * | 10/2017 | Nguyen | .............. | F16L 3/22 |
| 2018/0356032 A1 * | 12/2018 | Crider | .............. | F16M 13/022 |
| 2019/0234535 A1 * | 8/2019 | Reznar | .............. | F16L 3/237 |
| 2020/0052470 A1 * | 2/2020 | Matsuo | .............. | F16B 2/065 |
| 2020/0224685 A1 * | 7/2020 | Calhoun | .............. | G03B 17/56 |

FOREIGN PATENT DOCUMENTS

| | | |
|---|---|---|
| JP | H06-038342 | 2/1994 |
| JP | 2013-056114 A | 3/2013 |
| JP | 2014-180420 A | 9/2014 |

* cited by examiner

TUBE HOLDER

RELATED APPLICATIONS

This application is a continuation application of PCT/JP2017/018299 having an international filing date of May 16, 2017, which claims priority to Japanese Patent Application No. 2017-003216 filed on Jan. 12, 2017, the content of which is incorporated herein by reference.

BACKGROUND OF THE INVENTION

1. Field of the Invention

The present invention relates to a tube holder for holding various tubular items at medical sites and the like.

2. Description of the Related Art

The following is a holding tool for holding a tubular item used at a medical site near a patient or the like.

In the clip that is disclosed in Patent Document 1, for example, a pair of clamping portions are connected so as to respectively rotate by a rotation support portion, a first gripping portion gripping a patient's clothes is provided in the tip portion of the clamping portion, and a second gripping portion gripping a tube for dialysis or the like is provided between the first gripping portion and the rotation support portion. With this clip, it is possible to easily attach the tube by lightly pushing the tube into the second gripping portion and inserting the first gripping portion into the patient's clothes.

In the clamp that is disclosed in Patent Document 2, a tube gripping member is provided in a first handle portion, a tube is attached to the tube gripping member, and a second handle portion is openably and closably attached to the first handle portion by a spindle. The first handle portion and the second handle portion are capable of clamping a frame pipe of a bed by being biased in the closing direction by a torsion spring. As a result, the clamp is capable of holding the tube at a desired position in the frame pipe.

PRIOR ART DOCUMENTS

Patent Documents

Patent Document 1: Japanese Unexamined Patent Application Publication No. 2013-56114
Patent Document 2: U.S. Patent Publication No. 2013/0174838 A1

SUMMARY OF THE INVENTION

Technical Problem to be Solved by Invention

The clip and the clamp have no flexibility at parts to which tubes are attached and are limited by the diameters of attached tubular items. In neonatal care, in particular, a tube holder is required in using various syringes (such as injectors, washers, and droppers) for nutrition injection and so on and required in holding a patient circuit such as a respirator, and yet currently available products are incapable of meeting on-site needs in some cases.

The present invention has been made in view of such circumstances, and an object of the present invention is to provide a tube holder capable of holding tubular items of various sizes, that is, items with small and large diameters at medical sites.

Solution to Problem

A tube holder according to the present invention includes at least a set of clamping members having circular arc-shaped clamping concave portions, a spindle pivotably supporting end portions on one side along the circular arcs of the clamping members in a state where the clamping concave portions facing curvature center sides of the respective circular arcs face each other, and a biasing member pivoting and biasing end portions of the other side along the circular arc of the clamping member in a direction of mutual approaching. The clamping member is formed such that an inscribed circle formed between facing surfaces of the clamping concave portions is smaller than a virtual circle formed by extension of the circular arcs of the clamping concave portions in a state where a space between the other end portions is closed and the clamping concave portions are disposed on the same virtual circle formed by extension of the circular arcs in a state during opening and closing where the clamping members are pivoted and the end portions on the other side are moved close to and away from each other.

In the tube holder, the set of clamping members are pivoted and biased by the biasing member, and then the tip portions of the clamping members abut against each other and the clamping concave portions are closed. Once the clamping members are pivoted against the biasing force of the biasing member, the tip portions of the clamping members are separated from each other and the clamping concave portions are opened.

At a position during the opening and closing operation, the respective clamping concave portions are disposed on the same virtual circle. Accordingly, in the clamping concave portions of the clamping members in the closed state, the diameter of the inscribed circle formed between the facing surfaces of the clamping concave portions is smaller than the diameter of the virtual circle. When the clamping members are closed, parts less than half of the virtual circles overlap each other, and the overlapping parts constitute a substantially elliptical clamping space surrounded by the circular arcs. As a result, it is possible to fix, for example, a tube smaller in diameter than the virtual circle. In addition, when the clamping member is open at the maximum rotation angle, the clamping recess has a grippable maximum diameter larger than the diameter of the virtual circle. As described above, the clamping concave portion of the clamping member is capable of flexibly responding to tubular items of various sizes, that is, items smaller and larger in diameter than the virtual circle.

In the tube holder of the present invention, a fixed side clamping member fixed to a holder main body and a movable side clamping member pivotably supported on the holder main body by the spindle may constitute the set of clamping members, the fixed side clamping member may be fixed to the holder main body by a pair of fixed arm portions having the clamping concave portion being spaced apart in a direction along the spindle in a state where curvature centers of the respective circular arcs are aligned in the direction along the spindle, the movable side clamping member may be provided with a pair of movable arm portions having the clamping concave portion spaced apart in the direction along the spindle, and the fixed arm portion and the movable arm portion may be respectively disposed so as to be openable and closable in a front and a back in the direction along the spindle.

In the clamping member in the tube holder, the pair of fixed arm portions and the pair of movable arm portions respectively open and close the clamping concave portions in the front and the back in the direction along the spindle, and thus a tubular item is clamped in two places in a longitudinal direction. As a result, the inter-clamping distance can be increased, displacement of the held tubular item can be suppressed, and holding performance enhancement can be achieved.

In the tube holder of the present invention, the clamping member may be provided with two sets of a fixed side clamping member fixed to a holder main body and a movable side clamping member pivotably supported on the holder main body by the spindle, a pair of the fixed side clamping members may be fixed back to back to the holder main body in a state where curvature centers of the respective circular arcs face outward, and the movable side clamping member may be rotatably supported on the holder main body by the spindle in a state where a pair of the movable side clamping members faces respective outer sides of the pair of fixed side clamping portions with curvature centers of the respective circular arcs facing inward.

This tube holder is provided with the two sets of clamping members on the left and the right, and thus two tubular items can be held at the same time. The two tubular items of different diameters can be separately held in this case as each set of clamping members can be separately opened and closed.

In the tube holder of the present invention, the clamping member may be provided with two sets of a fixed side clamping member fixed to a holder main body and a movable side clamping member pivotably supported on the holder main body by the spindle, a pair of the fixed side clamping members may be fixed back to back to the holder main body in a state where curvature centers of the respective circular arcs face outward, the fixed side clamping member may be fixed to the holder main body by a pair of fixed arm portions having the clamping concave portion being spaced apart in a direction along the spindle in a state where curvature centers of the respective circular arcs are aligned in the direction along the spindle, the movable side clamping member may be rotatably supported on the holder main body by the spindle in a state where a pair of the movable side clamping members faces respective outer sides of the pair of fixed side clamping portions with curvature centers of the respective circular arcs facing inward, a pair of movable arm portions having the clamping concave portion may be spaced apart in the direction along the spindle, and the fixed arm portion and the movable arm portion may be respectively disposed so as to be openable and closable in a front and a back in the direction along the spindle.

This tube holder is capable of separately holding two tubular items of different diameters by means of the two sets of clamping members on the left and the right. In addition, each clamping member clamps the tubular item with the front and rear arm portions, and thus the tubular items can be stably held.

In the tube holder capable of holding two tubular items, a finger hooking piece extending to a side opposite to the fixed side clamping member may be formed between the fixed side clamping members, and the movable side clamping member may be provided with an operation piece at a position where the movable side clamping member is operable between the finger hooking piece and the movable side clamping member, in the holder main body.

This tube holder allows both clamping members to be easily opened in the opening direction by, for example, the finger hooking piece and the operation piece being sandwiched between the thumb and the index finger. The finger hooking piece extending from the holder main body can be used for any when the two sets of clamping, members on the left and the right are opened. As a result, the protruding part serving as a finger hook can be reduced and shape simplification and cost reduction can be achieved.

In this case, the operation piece may be in a connected state between the pair of movable arm portions and both movable arm portions can be opened and closed and the tubular item can be held with ease by single operation with respect to the operation piece.

In the tube holder of the present invention, a claw portion extending along the circular arc and an accommodating recess accommodating the claw portion when the clamping member is closed may be formed in the end portion on the other side of the clamping member.

When both clamping members are open to the maximum extent possible in the tube holder, the claw portions provided in the tip portions of the clamping members are in contact with the outer periphery of the tubular item. The extension length of the claw portion may be set so as to be capable of surrounding up to $2/3$ of the outer peripheral length of the tubular item that has an assumed maximum diameter. Accordingly, the tube holder is capable of holding a tubular item having a diameter larger than in a case where the claw portion is not provided. In the closed state, the claw portion is accommodated in the accommodating recess. Accordingly, the minimum diameter at which the clamping member is capable of performing clamping does not increase.

In the tube holder of the present invention, a plurality of projecting portions spaced apart in a direction along the circular arc may be formed in the clamping concave portion.

In the tube holder, the plurality of projecting portions are disposed along the outer circumferential direction of the tubular item when the clamping concave portion comes into contact with the outer peripheral surface of the tubular item. In a case where the tubular item is formed of an elastically deformable material, the projecting portions bite into the outer peripheral portion of the tubular item. Accordingly, a movement of the tubular item in the direction along the circular arc is regulated in the clamping concave portion. As a result, displacement of the held tubular item can be suppressed and holding performance enhancement can be achieved.

Advantageous Effects of Invention

With the tube holder of the present invention, it is possible to hold tubular items of various sizes, that is, items with small and large diameters at medical sites.

DETAILED DESCRIPTION OF THE PREFERRED EMBODIMENTS

Hereinafter, an embodiment of a tube holder of the present invention will be described with reference to accompanying drawings.

Figure 1:
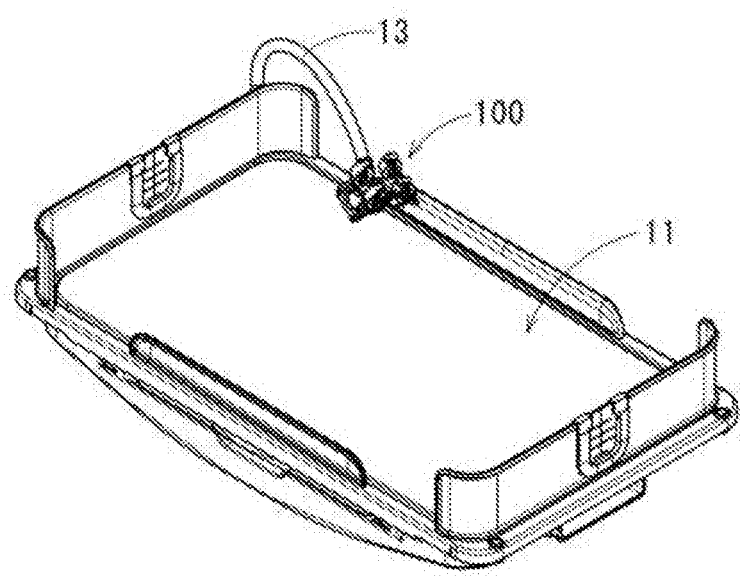
FIG. 1 is a perspective view of a bed of an incubator to which a tube holder according to an embodiment of the present invention is attached.

FIG. 1 is a perspective view of a bed of an incubator to which the tube holder according to the embodiment of the present invention is attached.

As illustrated in FIG. 1, a tube holder 100 according to the present embodiment can be preferably attached to, for example, a bed 11 of an incubator by means of a rod-shaped flexible arm 13. The flexible arm 13 has flexibility and is capable of supporting the tube holder 100 in a state where a bent shape is maintained in any direction. As a result, the tube holder 100 can be flexibly disposed at a desired position in a three-dimensional direction on the bed 11.

Figure 2:
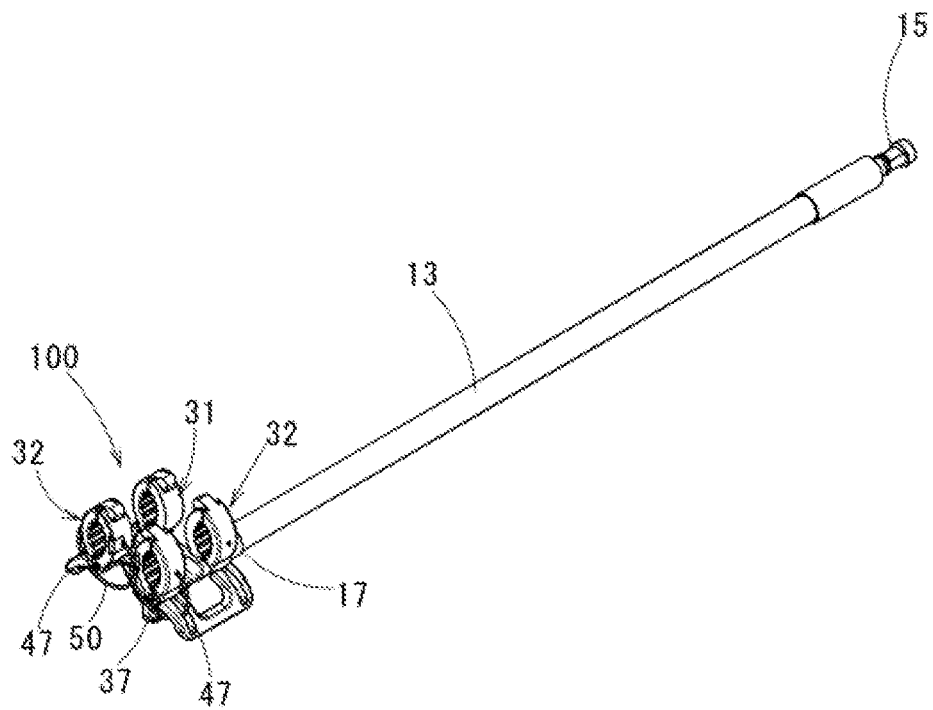
FIG. 2 is a perspective view of the tube holder illustrated in FIG. 1.
Figure 3:
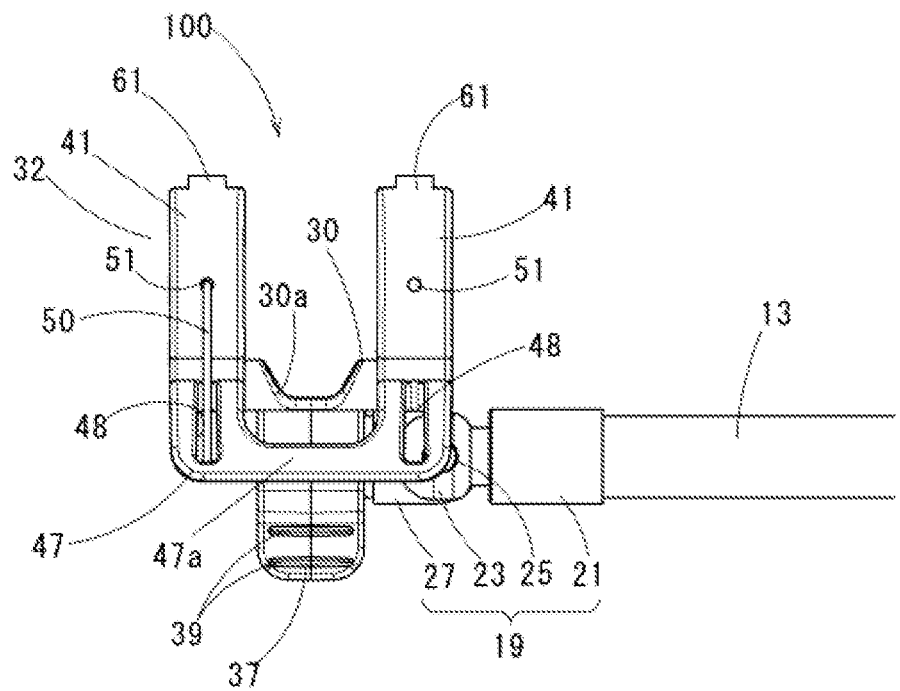
FIG. 3 is a side view of the main part of the tube holder illustrated in FIG. 2.
Figure 4:
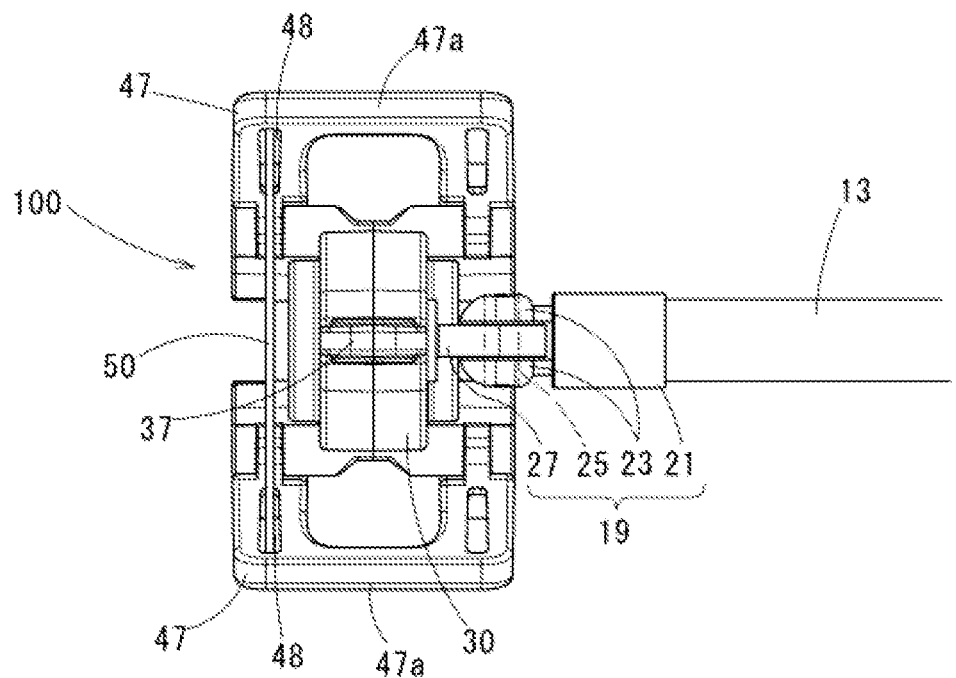
FIG. 4 is a bottom view of the main part of the tube holder illustrated in FIG. 2.

Specifically, the flexible arm 13 detachably supports the tube holder 100 interposed a joint portion 19 with a proximal end portion 15 detachably attached to the frame of the bed 11 and the joint portion 19 provided in a tip portion 17 as illustrated in FIGS. 2 to 4. The joint portion 19 has a fixed tube 21 in the tip portion 17. A pair of support pieces 23, which are supported by the fixed tube 21, are spaced apart from each other in the radial direction of the fixed tube 21. Between the support pieces 23, a swinging piece 27 is swingably clamped by a swinging shaft 25, which is in a direction orthogonal to the support pieces 23.

Figure 8:
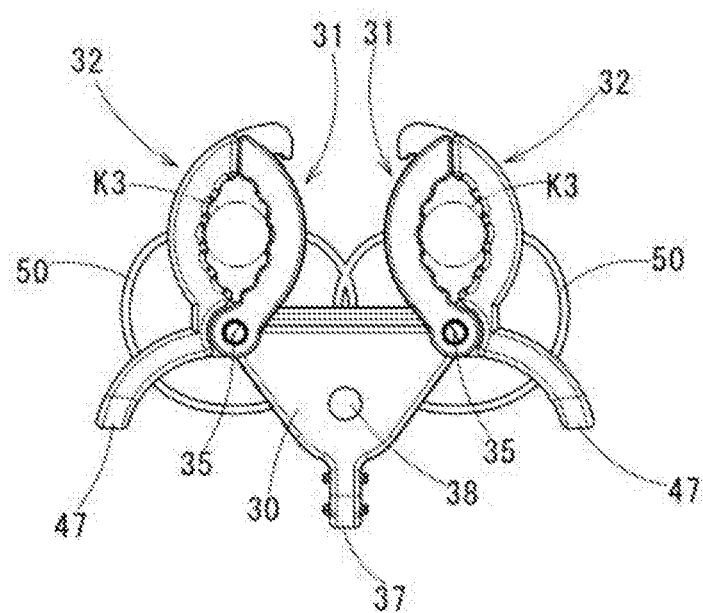
FIG. 8 is a rear view of the tube holder illustrated in FIG. 6.

An engagement shaft (not illustrated) protrudes at the swinging tip of the swinging piece 27. The engagement shaft is detachably attached to a support hole 38 (see FIG. 8), which is provided in a holder main body 30 of the tube holder 100. The tube holder 100 is supported by the tip portion 17 of the flexible arm 13 interposed the joint portion 19. As a result, the tube holder 100 is swingable at least in the direction of rotation that is about the swinging shaft 25. Assuming that the flexible arm 13 is linear, the tube holder 100 is swingable about the swinging shaft 25, which is orthogonal to the axial direction of the flexible arm 13.

In the present embodiment, the joint portion 19 may be a structure rotatably supporting the pair of support pieces 23 around the axis of the fixed tube 21. In this case, the joint portion 19 is capable of supporting the tube holder 100 in two degrees of freedom, one being the direction of swinging around the swinging shaft and the other being the direction of rotation around the axis of the fixed tube 21.

Figure 5:
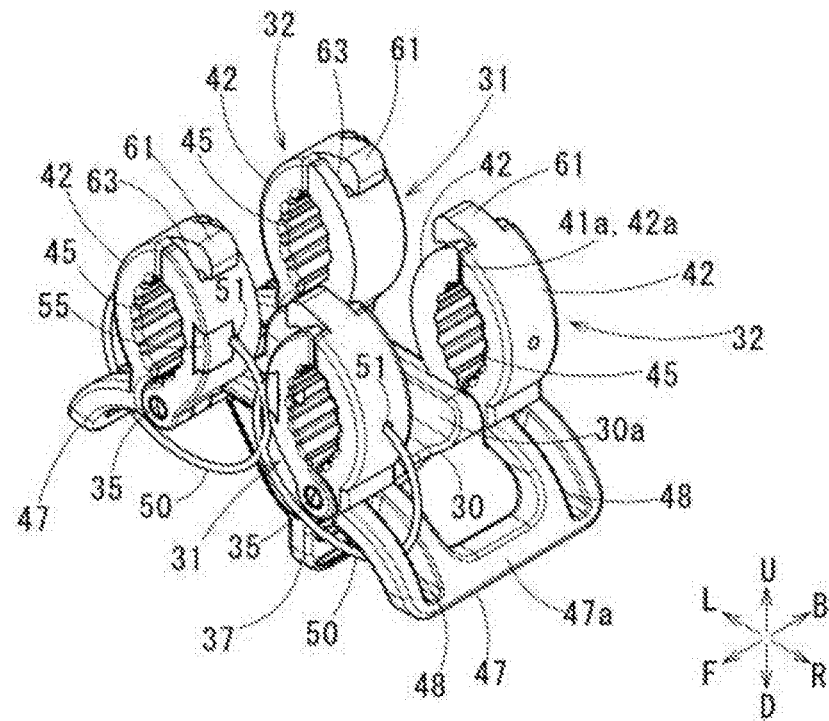
FIG. 5 is a perspective view of the tube holder that is closed.
Figure 6:
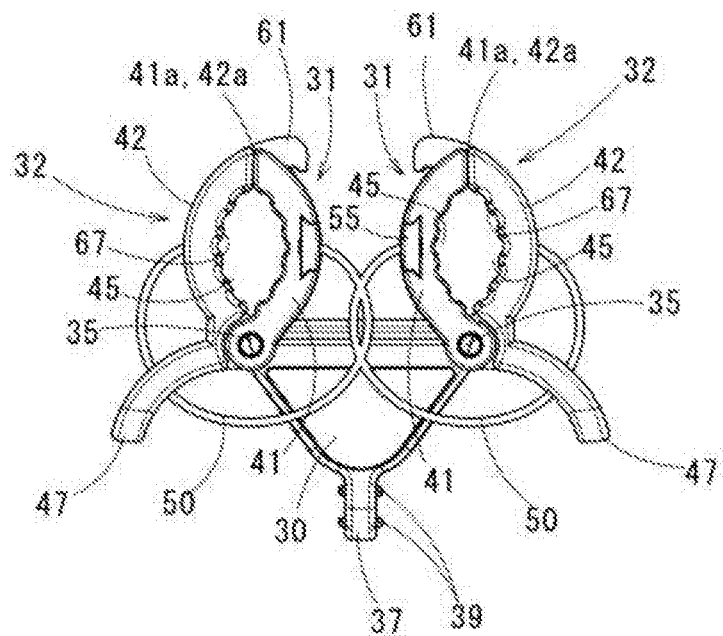
FIG. 6 is a front view of the tube holder illustrated in FIG. 5.
Figure 7:
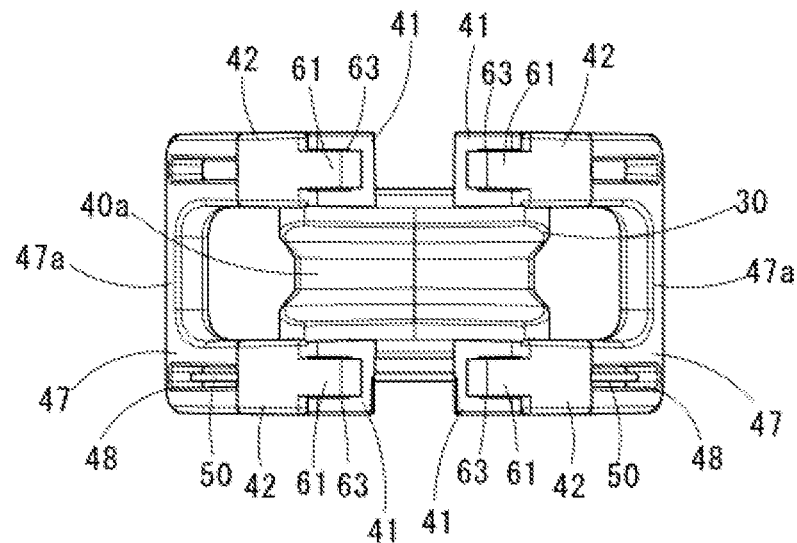
FIG. 7 is a plan view of the tube holder illustrated in FIG. 6.
Figure 9:
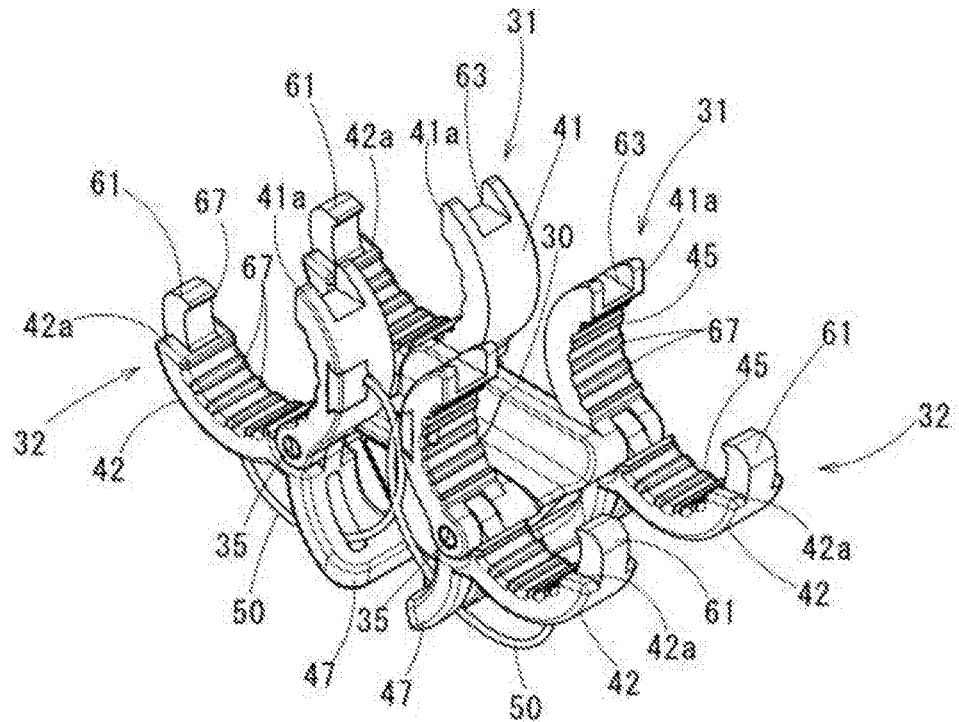
FIG. 9 is a perspective view of the tube holder that is open.
Figure 10:
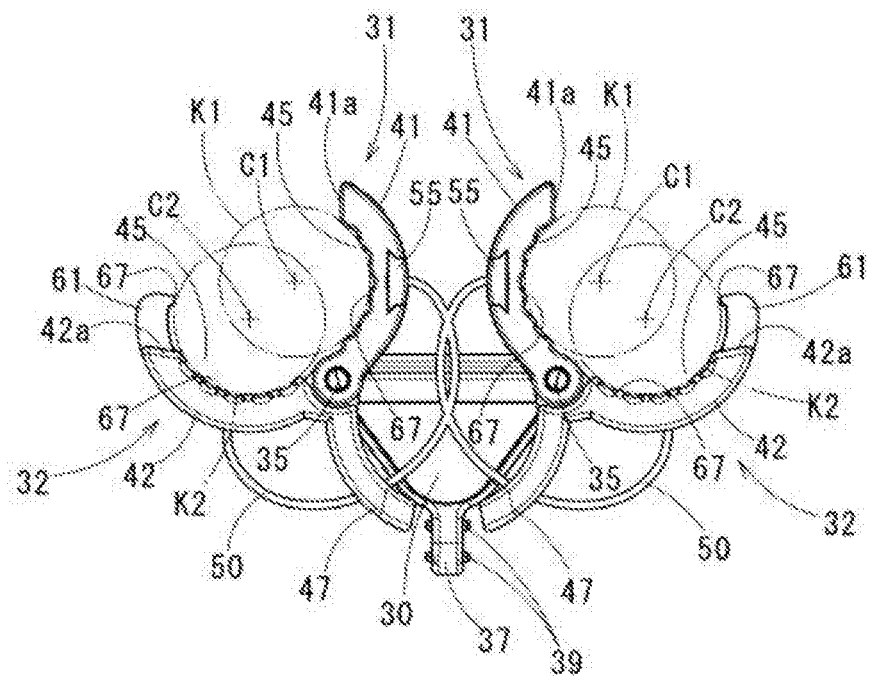
FIG. 10 is a front view of the tube holder that is open.
Figure 11:
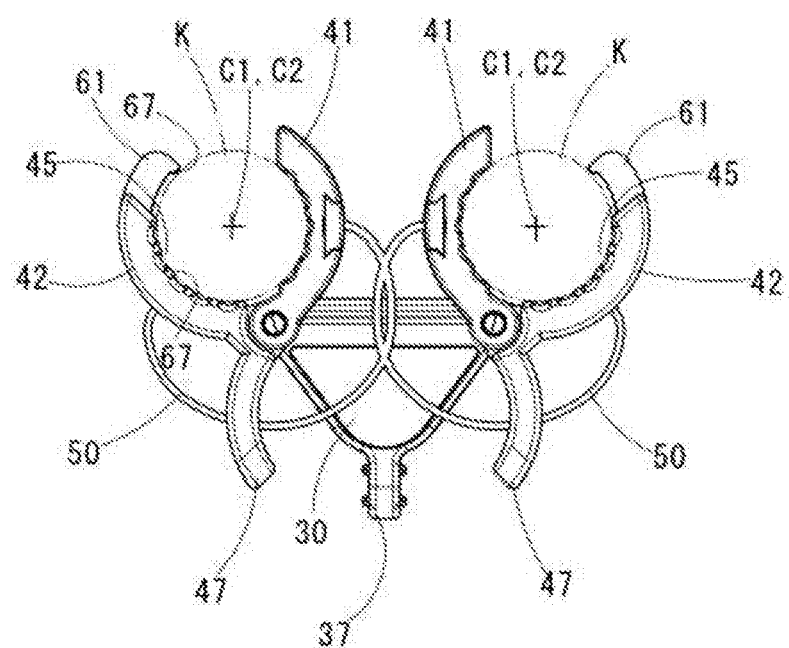
FIG. 11 is a front view of the tube holder during opening and closing.

The tube holder 100 that is closed is illustrated in FIGS. 5 to 8. The tube holder 100 that is fully open is illustrated in FIGS. 9 and 10. A state during opening and closing is illustrated in FIG. 11. As for the upward-downward, forward-rearward, and leftward-rightward directions in the present embodiment, the direction of the arrow U that is illustrated in FIG. 5 is the upward direction, the direction of the arrow D that is, illustrated in FIG. 5 is the downward direction, the direction of the arrow L that is illustrated in FIG. 5 is the leftward direction, the direction of the arrow R that is illustrated in FIG. 5 is the rightward direction, the direction of the arrow F that is illustrated in FIG. 5 is the forward direction, and the arrow B that is illustrated in FIG. 5 indicates the rearward direction.

The holder main body 30, a pair of clamping members 31 and 32, a spindle 35 supporting the clamping members 31 and 32 in an openable and closable manner, and a biasing member 50 biasing the clamping members 31 and 32 in the closing direction are the main elements that constitute the tube holder 100 of the present embodiment. In the present embodiment, a movable side clamping member 32 and a fixed side clamping member 31 integrally fixed to the holder main body 30 constitute the pair of clamping members 31 and 32.

The holder main body 30 is integrally injection-molded from, for example, polypropylene (PP). Each movable side clamping member 32 is integrally injection-molded from polypropylene (PP). The tube holder 100 uses the injection components whereas existing products have component configurations mainly based on machining, and thus the product cost of the tube holder 100 can be significantly reduced.

The holder main body 30 is formed in a substantially inverted triangle shape in front view and a laterally long and rectangular block shape in plan view. In the upper surface of the holder main body 30, a recessed groove 30a is formed along the leftward-rightward direction. At the lower end of the holder main body 30, a finger hooking piece 37, which will be described later, extends in a suspended state. The support hole 38 is formed at a substantially middle position on the back surface side of the holder main body 30. The engagement shaft (not illustrated) protruding from the swinging piece 27 of the flexible arm 13 is attached to the support hole 38.

The fixed side clamping member 31 that is fixed to the holder main body 30 and the movable side clamping member 32, which is openable and closable with respect to the fixed side clamping member 31, are respectively provided in both end portions of the holder main body 30 in the leftward-rightward direction. In other words, one set of the fixed side clamping member 31 and the movable side clamping member 32 is provided on each of the left and the right of the holder main body 30. Each of the clamping members 31 and 32 has arm portions 41 and 42 formed in a circular arc shape and having the same curvature, and is configured to be opened and closed in a state where clamping concave portions 45, which form a circular arc shape inside the arm portions 41 and 42, face each other. The arm portion in the fixed side clamping member 31 will be referred to as a fixed arm portion 41 and the arm portion in the movable side clamping member 32 will be referred to as a movable arm portion 42.

In this case, both fixed side clamping members 31 are disposed such that one end portion along the circular arc of the fixed arm portion 41 is fixed to both end portions of the holder main body 30 and curvature centers C1 (see FIG. 10) of the circular arcs of the fixed arm portions 41 are back to back toward the outside in the fixed state. In the movable side clamping member 32, an operation piece 47 is integrally provided in one end portion along the circular arc of the movable arm portion 42 so as to extend to the side that is opposite to the movable arm portion 42. The parts that are between the movable arm portions 42 and the operation pieces 47, are the end portions of the movable arm portions 42 described above, and are disposed so as to respectively face the fixed arm portions 41 from the outer sides with curvature centers C2 of the circular arcs of the movable arm portions 42 facing the inner sides, are pivotably supported on the holder main body 30 by the spindles 35.

In this state of attachment, the fixed arm portions 41 and the movable arm portions 42 are attached at both end positions of the C1 and C2 of the respective circular arcs parallel to each other and both clamping concave portions 45 facing each other and the spindles 35 are parallel to the curvature centers C1 and C2 of the circular arcs. In this state, the operation pieces 47 of both movable side clamping members 31 are disposed on the left and the right below the fixed arm portions 41 and the movable arm portions 42 and the finger hooking piece 37 integrated with the holder main body 30 is vertically disposed between the operation pieces 47. The finger hooking piece 37 is formed in a plate shape extending in the forward-rearward direction. Non-slip projecting ridges 39 extending in the forward-rearward direction are formed on the left and right plate surfaces of the finger hooking piece 37.

As a result, the fixed side clamping member 31 and the movable side clamping member 32 are operated in the directions of approaching and separation with gripping performed between the finger hooking piece 37 and the operation piece 47. As a result, the movable arm portion 42 is opened and closed with respect to the fixed arm portion 41, which is similar to scissors.

As illustrated in FIG. 5, in the present embodiment, the respective fixed arm portions 41 of the fixed side clamping members 31 have the same shape and are spaced apart from each other in the direction along the spindles 35 (forward-rearward direction) in the holder main body 30. Likewise, the respective movable arm portions 42 of the movable side clamping members 32 have the same shape and are spaced apart in the direction along the spindles 35 (forward-rearward direction). The operation pieces 47 are integrated by connecting portions 47a so as to connect the movable arm portions 42.

In this configuration, one fixed side clamping member 31 is provided on each of the left and the right and each of the fixed side clamping members 31 is provided with one fixed arm portion 41 in each of the front and the back. As a result, a total of four fixed arm portions 41 are provided. One movable side clamping member 32 is provided on each of the left and the right so as to correspond to the two fixed side clamping members 31. Each of the movable side clamping members 32 is provided with one movable arm portion 42 in each of the front and the back. As a result, a total of four movable arm portions 42 are provided. Each movable arm portion 42 is pivotably supported on the holder main body 30 by the spindle 35. Accordingly, a total of four spindles 35 are provided in the left, right, front, and back, the left spindles 35 are disposed on the same axis, and the right spindles 35 are disposed on the same axis.

In the tube holder 100, the movable side clamping member 32 pivots with respect to the fixed side clamping member 31. As a result, the respective, clamping concave portions 45 of the arm portions 41 and 42 can be opened and closed.

In this case, the respective clamping concave portions 45 of the arm portions 41 and 42 are formed by circular arcs having the same curvature radius. In addition, the respective clamping concave portions 45 of the fixed arm portion 41 of the fixed side clamping member 31 and the movable arm portion 42 of the movable side clamping member 32 that face each other are disposed on the same virtual circle K (see FIG. 11) at the positions during opening and closing where the movable side clamping members 32 pivot about the spindles 35 to move close to and away from the fixed side clamping members 31.

In other words, in the tube holder 100, the fixed side clamping member 31 and the movable side clamping member 32, which are a pair of clamping members, are formed such that an inscribed circle K3 (see FIG. 8) formed between the facing surfaces of the clamping concave portions 45 is smaller than virtual circles K1 and K2 formed by extension of the circular arcs of the clamping concave portions 45 in a state where the space between the opening and closing end portions (the other end portions of the present invention) is closed, the clamping concave portions 45 are disposed on the same virtual circle K formed by extension of the circular arcs in a state during opening and closing where the opening and closing end portions are moved close to and away from each other by pivoting of the movable side clamping member 32, which is one clamping member, and the opening and closing end portions can be further opened in the direction of separation from the state during opening and closing.

In the tube holder 100, the left and right movable arm portions 42 disposed on the front side in the left and right movable side clamping members 32 are biased in the closing direction by the biasing members 50. The movable arm portions 42 are integrated in the front and the back by the operation pieces 47, and thus the rear movable arm portions 42 are pivoted and biased in the same direction by the front movable arm portions 42 being biased.

The pair of biasing members 50 are disposed on the left and the right after being formed in a C shape from, for example, linear spring steel. The biasing members 50 are shaped so as to be integrally connected and fixed in the middle portions of the biasing members 50. The C-shaped biasing members 50 on the left and the right may be separate from each other or the biasing members 50 may be formed of a linear synthetic resin material.

An engagement hole 51 is formed in the outside surfaces of the fixed arm portion 41 and the movable arm portion 42. One end of the biasing member 50 is inserted into the engagement hole 51. The fixed arm portion 41 that is positioned on the front side of the fixed side clamping member 31 is provided with a piece member 55, which is detachable from the part of the engagement hole 51. The biasing member 50 that is inserted in the engagement hole 51 is locked by the piece member 55.

The elastic force of the biasing member 50 applies a preload that biases the closed movable side clamping member 32 further in the closing direction toward the fixed side clamping member 31.

In the operation piece 47 of the movable side clamping member 32, a rectangular long hole 48 through which the biasing member 50 is inserted is formed along the length direction of the operation piece 47. The biasing member 50 is inserted through the long hole 48. As a result, the biasing member 50 is disposed across the movable arm portion 42 of the movable side clamping member 32 and the fixed arm portion 41 of the fixed side clamping member 31 and interference with the operation piece 47 is prevented.

Although the biasing member 50 is provided between the fixed arm portion 41 and the movable arm portion 42 on the front side in the present embodiment, the engagement hole 51 and the long hole 48 are also provided in the fixed arm portion 41 and the movable arm portion 42 on the rear side, and thus the same biasing member 50 may be disposed between the fixed arm portion 41 and the movable arm portion 42 on the rear side in a case where an especially large biasing force is desired.

As illustrated in FIG. 5 and the like, claw portions 61 extending along a circular arc shape are formed in the opening and closing end portions of the respective movable arm portions 42 of the movable side clamping members 32. Accommodating recesses 63 accommodating the claw portions 61 are formed in the opening and closing end portions of the fixed arm portions 41 of the fixed side clamping members 31. As for the movable side clamping member 32 and the fixed side clamping member 31, a stopper surface 42a is formed at the proximal end position of the claw portion 61 of the movable arm portion 42, the stopper surface 42a and a stopper surface 41a formed on the tip surface of the fixed arm portion 41 abut against each other in the closed state, and the claw portion 61 is accommodated in the accommodating recess 63 in the abutting state.

A plurality of projecting portions 67, which are spaced apart from each other in the direction along the circular arc, are formed in the clamping concave portions 45 of the respective arm portions 41 and 42 Of the fixed side clamping member 31 and the movable side clamping member 32. The projecting portions 67 extend in the forward-rearward direction in the respective clamping concave portions 45. Groove-shaped recesses (reference numeral omitted) are formed between the projecting portions 67. As a result, the fixed side clamping member 31 and the movable side clamping member 32 are capable of regulating a movement of a tubular item in the direction along the circular arc by the projecting portions 67 abutting against a plurality of plate's on the outer peripheral surface of the tubular item sandwiched between the clamping concave portions 45. In a case where the tubular item is formed of an elastically deformable material, the projecting portions 67 bite into the outer peripheral portion of the tubular item and the tubular item can be reliably held. The projecting portion 67 is similarly formed at the tip of the claw portion 61 as well.

In the tube holder 100 configured as described above, the fixed side clamping member 31 and the movable side clamping member 32, which area pair of clamping members, are caused to approach each other against the biasing force of the biasing member 50 and with the finger hooking piece 37 and the operation piece 47 pinched with fingers from the state of being closed as illustrated in FIGS. 5 to 8. Then, the opening and closing end portions of the fixed arm portion 41 of the fixed side clamping member 31 and the movable arm portion 42 of the movable side clamping member 32 are separated from each other and the clamping concave portion 45 is opened as illustrated in FIGS. 9 and 10. As illustrated in FIG. 11, at this position during opening and closing, the circular arcs in the respective clamping concave portions 45 of the fixed arm portion 41 and the movable arm portion 42 are disposed so as to overlap the same (one) virtual circle K.

Accordingly, in the closed state of the fixed side clamping member 31 and the movable side clamping member 32, the diameter of the inscribed circle K3 (see FIG. 8) formed between the facing surfaces of the clamping concave portions 45 is smaller than the diameter of the virtual circle K (K1 and K2) (see FIG. 10), parts less than half of the virtual circles K1 and K2 overlap each other, and the overlapping parts constitute a substantially elliptical space surrounded by the circular arcs of the clamping concave portions 45. The short-axis-direction distance of this space is the diameter of the largest inscribed circle K3. Accordingly, a thin tubular item that is sufficiently smaller in diameter than virtual circle K can be held.

As illustrated in FIGS. 9 and 10, when the fixed side clamping member 31 and the movable side clamping member 32 are open at the maximum pivot angle, the maximum diameter at which clamping by the clamping concave portions 45 is possible exceeds the diameter of the virtual circle K described above, and thus a tubular item exceeding the diameter of the virtual circle K can be held.

In this case, the opening and closing end portions of the respective movable arm portions 42 of the movable side clamping members 32 are further provided with the claw portions 61, and thus the claw portions 61 abut against the outer peripheral surface of the tubular item at the maximum opening. The extension length of the claw portion 61 is set so as to be capable of surrounding up to ⅔ of the outer peripheral length of the tubular item that has an assumed maximum diameter. Accordingly, the tube holder 100 is capable of holding a tubular item having a diameter larger than in a case where the claw portion 61 is not provided.

As illustrated in FIG. 5 and the like, in a state where the fixed side clamping member 31 and the movable side clamping member 32 are closed, the claw portions 61 are accommodated in the accommodating recesses 63 of the respective fixed arm portions 41 of the fixed side clamping members 31, and thus interference with the fixed arm portion 41 can be avoided and the minimum diameter of the tubular item that can be clamped can be maintained without the substantially elliptical space being expanded.

As a result, the clamping concave portions 45 of the fixed side clamping member 31 and the movable side clamping member 32 are capable of flexibly responding to tubular items of various sizes, that is, items smaller and larger in diameter than the virtual circle K.

The movable side clamping members 32 are disposed so as to respectively face the pair of fixed side clamping members 31, and thus the tube holder 100 is capable of holding two tubular items at the same time. Two tubular items of different diameters can be independently held in this case as the pair of movable side clamping members 32 are separate bodies.

The two arm portions 41 and 42 are spaced apart from each other in the direction along the spindle 35 (forward-rearward direction) in the fixed side clamping member 31 and the movable side clamping member 32 alike, and thus the pair of front and rear clamping concave portions 45 (four clamping concave portions 45 in total) are opened and closed by the arm portions 41 and 42. Accordingly, two tubular items held on the left and the right are clamped in two places separated in a longitudinal direction. As a result, wobbling of the held tubular items can be suppressed and holding performance enhancement can be, achieved.

Accordingly, the tube holder 100 is capable of holding tubular items of various sizes, that is, items with small and large diameters with high holding performance at medical sites.

The present invention is not limited to the above embodiment, and various modifications can be made without departing from the spirit of the present invention.

In the embodiment, the fixed side clamping member 31 and the movable side clamping member 32 are provided in two sets on the left and the right. One set is possible in an alternative configuration. In the embodiment, each of the fixed side clamping member 31 and the movable side clamping member 32 is provided with two arm portions spaced apart from each other in the forward-rearward direction. The number of the arm portions may be one in an alternative configuration. In any of the embodiments, the claw portions 61 extending along the circular arc and the accommodating recesses 63 accommodating the claw portions 61 when the clamping members 31 and 32 are closed may be formed in the end portions of the fixed side clamping member 31 and the movable side clamping member 32.

INDUSTRIAL APPLICABILITY

It is possible to provide a tube holder capable of holding tubular items of various sizes, that is, items with small and large diameters at medical sites.

What is claimed is:

1. A tube holder comprising:
   at least a set of clamping members having circular arc-shaped clamping concave portions;
   a spindle pivotably supporting end portions on one side along the circular arcs of the clamping members in a state where the clamping concave portions facing curvature center sides of the respective circular arcs face each other; and
   a biasing member pivoting and biasing end portions of the other side along the circular arc of the clamping member in a direction of mutual approaching,
   wherein the clamping member is formed such that an inscribed circle formed between facing surfaces of the clamping concave portions is smaller than a virtual circle formed by extension of the circular arcs of the clamping concave portions in a state where a space between the other end portions is closed and the clamping concave portions are disposed on the same virtual circle formed by extension of the circular arcs in a state during opening and closing where the clamping members are pivoted and the end portions on the other side are moved close to and away from each other,
   a claw portion extending along the circular arc and an accommodating recess accommodating the claw portion when the clamping member is closed are formed in each the end portions on the other side of the clamping members, and
   a plurality of projecting portions spaced apart in a direction along the circular arc are formed in the clamping concave portion including a tip of the claw portion.

2. The tube holder according to claim 1,
   wherein the set of clamping members consists of a fixed side clamping member fixed to a holder main body and a movable side clamping member pivotably supported on the holder main body by the spindle, the fixed side clamping member is fixed to the holder main body by a pair of fixed arm portions having the clamping concave portion being spaced apart in a direction along the spindle in a state where curvature centers of the respective circular arcs are aligned in the direction along the spindle, the movable side clamping member is provided with a pair of movable arm portions having the clamping concave portion spaced apart in the direction along the spindle, and the fixed arm portion and the movable arm portion are respectively disposed so as to be openable and closable in a front and a back in the direction along the spindle.

3. The tube holder according to claim 1,
   wherein the clamping member is provided with two sets of a fixed side clamping member fixed to a holder main body and a movable side clamping member pivotably supported on the holder main body by the spindle, a pair of the fixed side clamping members is fixed back to back to the holder main body in a state where curvature centers of the respective circular arcs toward outward, and the movable side clamping member is rotatably supported on the holder main body by the spindle in a state where a pair of the movable side clamping members faces respective outer sides of the pair of fixed side clamping portions with curvature centers of the respective circular arcs toward inward.

4. The tube holder according to claim 1,
   wherein the clamping member is provided with two sets of a fixed side clamping member fixed to a holder main body and a movable side clamping member pivotably supported on the holder main body by the spindle, a pair of the fixed side clamping members is fixed back to back to the holder main body in a state where curvature centers of the respective circular arcs toward outward, the fixed side clamping member is fixed to the holder main body by a pair of fixed arm portions having the clamping concave portion being spaced apart in a direction along the spindle in a state where curvature centers of the respective circular arcs are aligned in the direction along the spindle, the movable side clamping member is rotatably supported on the holder main body by the spindle in a state where a pair of the movable side clamping members faces respective outer sides of the pair of fixed side clamping portions with curvature centers of the respective circular arcs toward inward, a pair of movable arm portions having the clamping concave portion is spaced apart in the direction along the spindle, and the fixed arm portion and the movable arm portion are respectively disposed so as to be openable and closable in a front and a back in the direction along the spindle.

5. The tube holder according to claim 2,
   wherein a finger hooking piece extending to a side opposite to the fixed side clamping member is formed between the fixed side clamping, members in the holder main body, and an operation piece is provided at a position where the movable arm portion is operable between the finger hooking piece and the operation piece, in the movable side clamping member.

6. The tube holder according to claim 5,
   wherein the operation piece is in a connected state between the pair of movable arm portions.

7. The tube holder according to claim 4,
   wherein a finger hooking piece extending to a side opposite to the fixed side clamping member is formed between the fixed side clamping members in the holder main body, and an operation piece is provided at a position where the movable arm portion is operable between the finger hooking piece and the operation piece, in the movable side clamping member.

8. The tube holder according to claim 7,
   wherein the operation piece is in a connected state between the pair of movable arm portions.

* * * * *